(12) United States Patent
Park et al.

(10) Patent No.: US 7,741,101 B2
(45) Date of Patent: Jun. 22, 2010

(54) ESCHERICHIA STRAIN CAPABLE OF CONVERTING XMP TO GMP AND MAINTAINING THE INACTIVATED STATE OF GENE(S) ASSOCIATED WITH GMP DEGRADATION AND METHODS OF USING THE SAME

(75) Inventors: Young-hoon Park, Seongnam (KR); Hyoung-suk Kim, Seoul (KR); Jin-nam Lee, Seoul (KR); Ko-hoon Oh, Seoul (KR); Jeong-hwan Kim, Seoul (KR); Yoon-suk Oh, Kyungki-do (KR); Jae-ick Sim, Kyungki-do (KR); Kyung-oh Choi, Busan (KR)

(73) Assignee: CJ Cheiljedang Corporation, Seoul (KR)

( * ) Notice: Subject to any disclaimer, the term of this patent is extended or adjusted under 35 U.S.C. 154(b) by 250 days.

(21) Appl. No.: 11/814,417

(22) PCT Filed: Jan. 20, 2006

(86) PCT No.: PCT/KR2006/000221

§ 371 (c)(1),
(2), (4) Date: Jul. 20, 2007

(87) PCT Pub. No.: WO2006/078132

PCT Pub. Date: Jul. 27, 2006

(65) Prior Publication Data

US 2008/0299620 A1    Dec. 4, 2008

(30) Foreign Application Priority Data

Jan. 21, 2005    (KR)    ............ 10-2005-0005863

(51) Int. Cl.
| | | |
|---|---|---|
| *C12N 1/21* | (2006.01) | |
| *C12P 19/30* | (2006.01) | |
| *C12P 21/00* | (2006.01) | |
| *C12N 9/00* | (2006.01) | |
| *C12N 15/09* | (2006.01) | |

(52) U.S. Cl. .................... 435/252.33; 435/89; 435/183; 435/471; 435/69.1

(58) Field of Classification Search ............ 435/252.33, 435/471, 89
See application file for complete search history.

(56) References Cited

FOREIGN PATENT DOCUMENTS

| EP | 1170370 | 1/2002 |
|---|---|---|
| KR | 2000-0040839 | 7/2000 |
| KR | 2001/0021986 | 3/2001 |
| KR | 2002/0004870 | 1/2002 |
| KR | 2005/0062027 | 6/2005 |
| WO | WO99/03988 | 1/1999 |

OTHER PUBLICATIONS

Golovan et al., Canadian Journal of Microbiology 46:59-71, 2000.*
UniProt accession No. P36766 , Oct. 1, 2004.*

* cited by examiner

*Primary Examiner*—Delia M Ramirez
(74) *Attorney, Agent, or Firm*—Occhiuti Rohlicek & Tsao LLP

(57) ABSTRACT

Provided are mutant strains derived from *Escherichia* sp. GPU1114 (Accession No. KCCM-10536), having cumulative inactivation of deoD, aphA, appA, and hprt genes, and methods of using the same.

10 Claims, 8 Drawing Sheets

ESCHERICHIA STRAIN CAPABLE OF CONVERTING XMP TO GMP AND MAINTAINING THE INACTIVATED STATE OF GENE(S) ASSOCIATED WITH GMP DEGRADATION AND METHODS OF USING THE SAME

CROSS-REFERENCE TO RELATED APPLICATIONS

This application is the National State of International Application No. PCT/KR2006/000221, filed on Jan. 20, 2006, which claims the benefit of Korean Application Serial No. 10-2005-0005863, filed on Jan. 21, 2005. The contents of both of the foregoing applications are hereby incorporated by reference in their entirety.

TECHNICAL FIELD

The present invention relates to an *Escherichia* strain capable of converting 5'-xanthylic acid (XMP) to 5'-guanylic acid (GMP) and maintaining the inactivated state of a gene(s) associated with GMP degradation, and methods of using the same.

BACKGROUND ART

5'-guanylic acid (GMP) can be produced by microbial enzymatic or chemical breakdown of yeast RNA, direct fermentation for directly producing nucleotides using mutant strains cultured in media containing a sugar, a nitrogen source, and a phosphate source, or a combination method including the fermentative synthesis of nucleotide intermediates and the chemical or enzymatic conversion of the nucleotide intermediates to nucleotides. In recent years, a combination method that combines fermentative or chemical synthesis and enzymatic conversion is industrially widely used due to its economical advantages.

GMP production by the combination method consists of fermentative synthesis of 5'-xanthylic acid (XMP) and enzymatic conversion of XMP to GMP. At this time, two types of microbial strains are used. That is, an XMP-producing strain is used in the fermentative synthesis, and a microbial strain capable of inducing a continuous high-level expression of a gene encoding XMP aminase activity is used in the enzymatic conversion. In this case, the survival rate of the microbial strain used in the enzymatic conversion is remarkably reduced during a later culture period relative to during an initial culture period, thereby decreasing the production of GMP. Furthermore, it is known that the guaA gene encoding XMP aminase is fatal to host cells, and thus, the continuous high-level expression of XMP aminase hinders the growth of the microbial strain used in the enzymatic conversion during the later culture period. In addition, it is known that an internal gene responsible for GMP degradation in the microbial strain used for the enzymatic conversion is expressed, thereby facilitating the degradation of GMP.

In view of the above problems, the present inventors developed *Escherichia* sp. GPD1114 (Accession No. KCCM-10543) including an XMP aminase-encoding gene capable of expressing XMP aminase according to cellular growth state and an inactivated internal glnL gene. Furthermore, the present inventors developed *Escherichia* sp. GPU1114 (Accession No. KCCM-10536) derived from the *Escherichia* sp. GPD1114, in which the ushA gene encoding 5'-nucleotidase is inactivated to remove GMP degradability.

However, since the *Escherichia* sp. GPU1114 still contains internal genes associated with GMP degradation except the ushA gene encoding 5'-nucleotidase, GMP can be degraded into guanosine or guanine. Therefore, a microbial strain with simultaneous inactivation of all genes associated with GMP degradation is required in the art.

DISCLOSURE OF INVENTION

Technical Problem

The present invention provides a microbial strain capable of converting 5'-xanthylic acid (XMP) to 5'-guanylic acid (GMP) and maintaining the inactivated state of an internal gene(s) associated with GMP degradation.

The present invention also provides a method of accumulating GMP synthetase in a high concentration in a culture medium using the microbial strain.

The present invention also provides a method of producing GMP, guanosine 5'-diphosphate (GDP), or guanosine 5'-triphosphate (GTP) using the microbial strain.

Technical Solution

The present invention provides a strain of the genus *Escherichia* which is derived from *Escherichia* sp. GPU1114 (Accession No. KCCM-10536) and includes an inactivated deoD gene.

The parent strain, *Escherichia* sp. GPU1114 (Accession No. KCCM-10536) is an *Escherichia coli* (*E. coli*) strain in which glnL gene is inactivated, guaA gene encoding 5'-xanthylic acid (XMP) aminase is inserted by transformation, and an internal ushA gene encoding 5'-nucleotidase is inactivated. In the *Escherichia* sp. GPU1114 (Accession No. KCCM-10536), XMP can be converted to 5'-guanylic acid (GMP) at a high level by the expression of the guaA gene, and GMP degradation activity is low due to no expression of the ushA gene, thereby increasing GMP productivity.

As used herein, the deoD gene is not limited provided that it is a gene encoding purine-nucleoside phosphorylase activity. For example, the deoD gene may be NCBI accession no. NP_418801, but the present invention is not limited thereto. Thus, the deoD gene is meant to embrace a wild-type gene and a natural or artificial mutant gene for deoD.

The *Escherichia* strain of the present invention may be *E. coli* DKO-ud (Accession No. KCCM-10633).

The present invention also provides a strain of the genus *Escherichia* which is derived from *Escherichia* sp. GPU1114 (Accession No. KCCM-10536) and includes inactivated deoD and aphA genes.

The aphA gene is not limited provided that it is a gene encoding acid phosphatase activity. For example, the aphA gene may be NCBI accession no. NP_418-479, but the present invention is not limited thereto. Thus, the aphA gene is meant to embrace a wild-type gene and a natural or artificial mutant gene for aphA.

The *Escherichia* strain of the present invention may be *E. coli* TKO-udh (Accession No. KCCM-10631).

The present invention also provides a strain of the genus *Escherichia* which is derived from *Escherichia* sp. GPU1114 (Accession No. KCCM-10536) and includes inactivated deoD, aphA, and appA genes.

The appA gene is not limited provided that it is a gene encoding acid (poly)phosphatase activity. For example, the appA gene may be NCBI accession no. NP_415500, but the present invention is not limited thereto. Thus, the appA gene is meant to embrace a wild-type gene and a natural or artificial mutant gene for appA.

The *Escherichia* strain of the present invention may be *E. coli* QKO-udhp (Accession No. KCCM-10632).

The present invention also provides a strain of the genus *Escherichia* which is derived from *Escherichia* sp. GPU1114 (Accession No. KCCM-10536) and includes inactivated deoD, aphA, appA, and hprt genes.

The hprt gene is not limited provided that it is a gene encoding hypoxanthine phosphoribosyltransferase. For example, the hprt gene may be NCBI accession no. NP_414667, but the present invention is not limited thereto. Thus, the hprt gene is meant to embrace a wild-type gene and a natural or artificial mutant gene for hprt.

The *Escherichia* strain of the present invention may be *E. coli* QIKO (Accession No. KCCM-10630).

As used herein, the term 'inactivation' indicates that a target gene is not expressed, or even if the expression is possible, the gene does not produce a functional gene product. The 'inactivation' embraces the meaning that a target gene is completely inactivated or is not substantially expressed due to its significantly low expression level.

In the *Escherichia* strains of the present invention, the inactivated genes can be obtained by any method known in the art, e.g., site-specific mutagenesis or homologous recombination, but the present invention is not limited thereto. Homologous recombination is preferable. The inactivation of a gene can be induced by deletion, substitution, inversion, or a combination thereof, but the present invention is not limited thereto.

Gene inactivation by homologous recombination includes constructing inactivated gene cassettes by inserting foreign DNAs into target genomic DNA fragments, inserting the cassettes into microbial strains to induce homologous recombination between internal genes in the microbial cells and the cassettes, and selecting recombinant strains containing inactivated genes. For convenience, the foreign DNAs cloned into the target DNAs may contain a selectable marker, e.g., an antibiotic resistance gene. Target genes inactivated with antibiotic resistance gene-containing cassettes can be easily selected on an antibiotic-containing agar plate. Occurrence of recombination can be confirmed by southern blotting, PCR (polymerase chain reaction), etc.

In the case of using inactivated cassettes containing antibiotic resistance genes during the preparation of the *Escherichia* strains of the present invention, it is preferable to remove the antibiotic resistance genes after selection is completed. For example, the removal of antibiotic resistance genes from selected strains includes transforming the selected strains with plasmids expressing genes capable of recognizing specific nucleotide sequences of inactivated cassettes and removing antibiotic resistance genes; and removing antibiotic resistance genes from the transformants. The resultant antibiotic resistance gene-free transformants can be selected on an ampicillin-containing agar plate. The removal of antibiotic resistance genes from target DNAs can be confirmed by colony transfer onto an agar plate containing an appropriate antibiotic with a toothpick and growth of colonies on the agar plate.

The *Escherichia* strains of the present invention can be prepared using the following illustrative methods.

Genomic DNAs are extracted from *Escherichia* sp. GPU1114 (KCCM-10536), and deoD, aphA, appA, and hprt genes are amplified by PCR using the genomic DNAs as templates. The deoD, aphA, appA, and hprt genes are cloned into plasmids or other vectors to construct recombinant vectors (e.g., recombinant plasmids pDEO, pAPH, pAPP, pHPRT). Host cells such as *E. coli* cells are transformed with the recombinant vectors. After the transformants are cultured, recombinant vectors containing the deoD, aphA, appA, and hprt genes are extracted from the transformed cells. A loxp-containing antibiotic resistance gene fragment is inserted into the deoD, aphA, appA, and hprt genes of the recombinant vectors to construct recombinant vectors containing inactivated deoD, aphA, appA, and hprt genes (e.g., pTdeoD:loxpKAT, pTaphA:loxpKAT, pTappA:loxpKAT, pThprt:loxpCAT). The recombinant vectors are inserted in host cells and cultured. After the culture, recombinant vectors are extracted from the transformants and digested with appropriate restriction enzymes to obtain deoD, aphA, appA, and hprt gene-inactivated cassette fragments (e.g., Δ deoD:loxpKAT, Δ aph:loxpKAT, Δ app:loxpKAT, Δ hprt:loxpCAT). First, Δ deoD:loxpKAT is inserted into the GMP-producing strain GPU1114 by electroporation, etc., and the transformed GMP-producing strain GPU1114 is maintained under the antibiotic selection pressure to allow recombination between an antibiotic marker-containing deoD gene fragment and a chromosomal wild-type deoD gene to occur, thereby obtaining recombinant strains maintaining the inactivated state of the deoD gene even when generation continues. To further inactivate the aphA gene in the selected recombinant strains, the antibiotic marker must be removed. For this, recombinant vectors expressing genes recognizing loxp sites in antibiotic resistance genes and removing the antibiotic resistance genes are inserted into the selected recombinant strains by electroporation, etc. The selection of the resultant transformants is performed on an ampicillin-containing agar plate using acquired antibiotic resistance. The removal of antibiotic resistance genes from target DNAs can be confirmed by colony transfer onto an agar plate containing an appropriate antibiotic with a toothpick and growth of colonies on the agar plate. The resultant transformants are maintained under the antibiotic selection pressure to allow recombination between a deoD gene fragment containing a part of the antibiotic marker and a chromosomal wild-type deoD gene to occur, thereby obtaining transformed strains (e.g., *E. coli* DKO-ud) maintaining the inactivated state of the ushA and deoD genes even when generations are continued. When the above-described procedure is sequentially applied to the aphA, appA, and hprt genes, transformed strains with cumulative inactivation of the deoD, aphA, appA, and hprt genes can be obtained.

The present invention also provides a method of accumulating GMP synthetase in cells, which includes culturing an *Escherichia* strain of the present invention.

The present invention also provides a method of producing GMP, guanosine 5'-diphosphate (GDP), or guanosine 5'-triphosphate (GTP), which includes culturing an *Escherichia* strain of the present invention.

In the methods of the present invention, the culturing of the *Escherichia* strain of the present invention can be performed under commonly known culture conditions, e.g., in a culture medium containing a carbon source, a nitrogen source, an amino acid, an inorganic compound, etc., while adjusting the temperature and pH of the culture medium.

The carbon source may be a carbohydrate such as glucose, fructose, or sterilized molasses (i.e., molasses converted to reducing sugar), and the nitrogen source may be an inorganic nitrogen source such as ammonia, ammonium chloride, and ammonium sulfate, and an organic nitrogen source such as peptone, NZ-amine, meat extract, yeast extract, corn steep liquor, casein hydroxylate, fish meal or its digest, defatted soybean or its digest. The inorganic compound may be potassium hydrogen phosphate, potassium dihydrogen phosphate, magnesium sulfate, iron sulfate, manganese sulfate, calcium carbonate, etc. When needed, the culture medium may be supplemented with vitamins, bases, etc. The culture may be performed under an aerobic condition, e.g., by shaking or aerobic stirring, preferably at a temperature of 30 to 40° C. The pH of the culture medium may be maintained near neutral. The culture may be performed for 1 to 2 days so that products having XMP aminase activity are accumulated in the culture medium.

In the present invention, GMP can be produced by converting XMP to GMP using GMP synthetase produced by the culture of an *Escherichia* strain according to the present invention. The conversion of XMP to GMP can be achieved by adding a material (e.g., xylene) increasing the cell membrane permeability of XMP into a culture medium so that XMP is introduced into a GMP-producing strain. The material increasing the cell membrane permeability of XMP is well known in the art, e.g., a hydrophobic material (e.g., xylene, toluene, benzene, ethyl acetate), a surfactant (e.g., polyoxyethylenestearylamine (e.g., Nymeen S-215, Nihon Yushi Co.) a cationic surfactant such as cetyltrimethylammonium bromide, Cation FB, or Cation F2-40E, or an anionic surfactant such as sodium oleylamide sulfate, Newrex TAB, and Rapizole 80), a metal ion (e.g., calcium ion, magnesium ion), but the present invention is not limited to the above-illustrated examples. The content of the material increasing the cell membrane permeability of XMP varies according to the type of the material, and can be appropriately adjusted by those of ordinary skill in the art. For example, xylene may be used in an amount of 0.5 to 1 wt % based on the total weight of a culture medium. In addition, GDP or GTP can be produced by commonly known enzymatic or chemical phosphorylation of GMP.

DESCRIPTION OF DRAWINGS

The above and other features and advantages of the present invention will become more apparent by describing in detail exemplary embodiments thereof with reference to the attached drawings in which.

BEST MODE

Hereinafter, the present invention will be described more specifically with reference to the following Examples. The following Examples are for illustrative purposes and are not intended to limit the scope of the invention.

EXAMPLES

Example 1

Construction of Recombinant Plasmid and Inactivation of deoD Gene Using the Recombinant Plasmid About 720 bp DNA fragments containing the open reading frames (ORFs) of deoD genes were amplified by PCR using genomic DNAs of *E. coli* GPU1114 (Accession No. KCCM-10536) as templates and oligonucleotides as set forth in SEQ ID NOS: 1 and 2 as primers. The PCR was performed at 94° C. for 30 seconds for denaturation, 50° C. for 30 seconds for annealing, and 68° C. for 1 minute and 30 seconds for extension for 35 cycles.

Figure 1A:
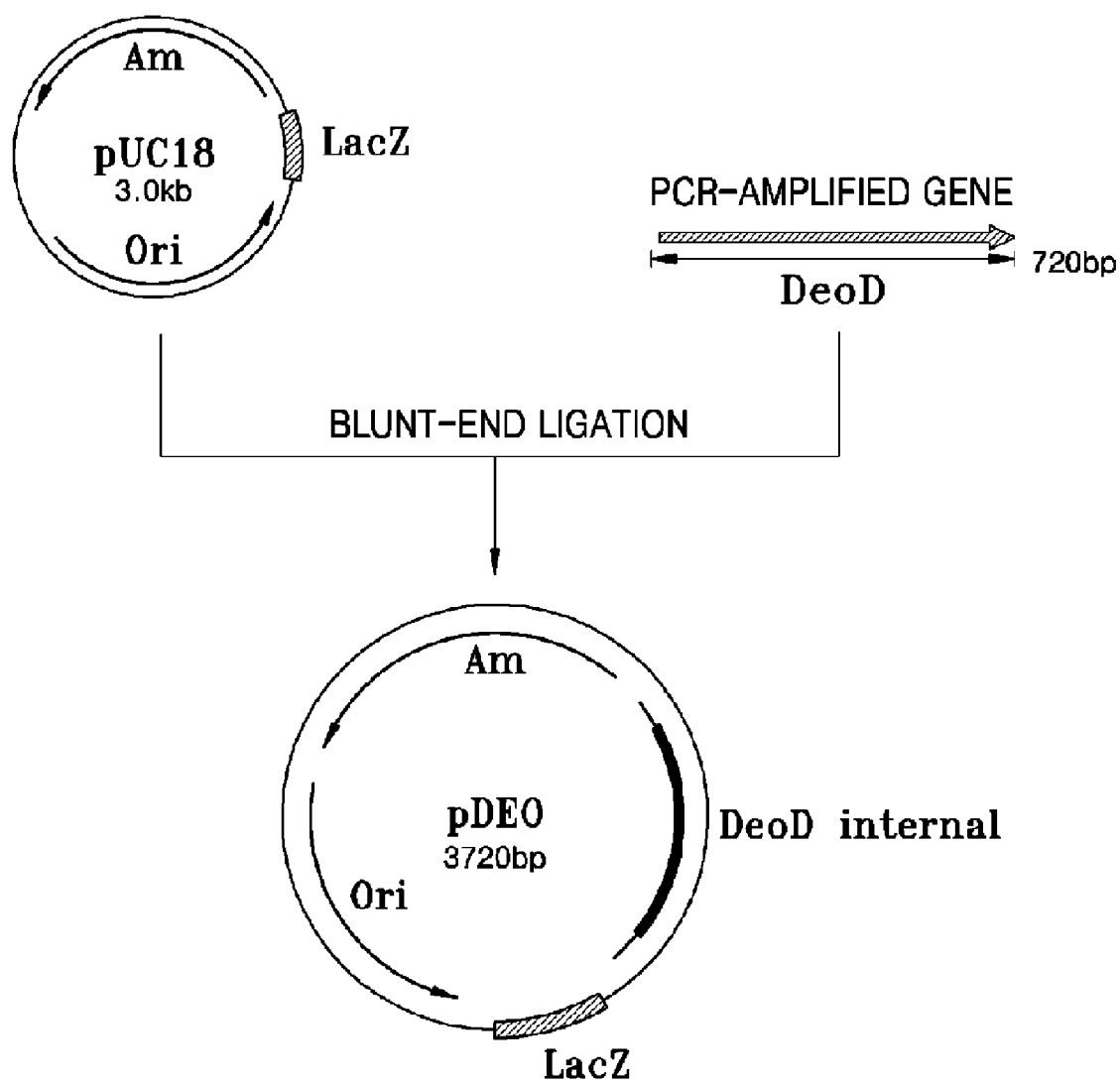
FIG. 1A is a scheme of the construction of a recombinant plasmid pDEO of Example 1 of the present invention.

After the PCR products were size-fractionated by 0.1% agarose gel electrophoresis, bands containing 720 bp DNA fragments were purified. The DNA fragments were ligated into the HindII site of pUC18 cloning vectors (Promega Co.) at 16° C. overnight (see FIG. 1A). The resultant recombinant plasmids pDEO were transformed into *E. coli* DH5 α, the obtained transformants were smeared onto solid media containing ampicillin (50 mg/L) and cultured at 37° C. overnight.

Figure 1B:
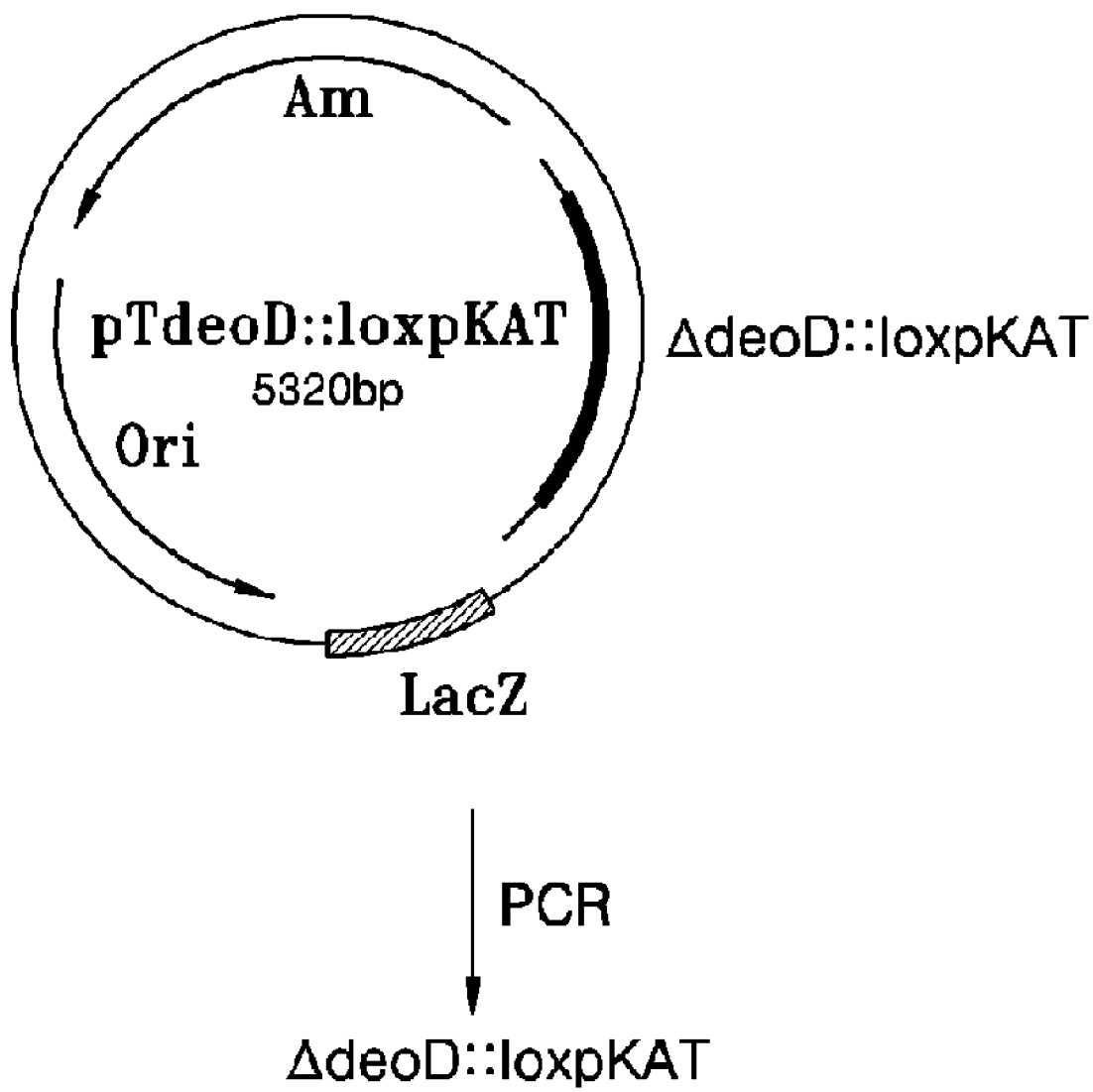
FIG. 1B is a scheme of the construction of a recombinant plasmid pTdcoD:loxpKAT of Example 1 of the present invention.

Colonies grown on the solid media were inoculated by loop transfer needles onto 3 mL of ampicillin-containing liquid media and cultured overnight. Then, plasmid DNAs were isolated using a QIAGEN mini prep kit (QIAGEN) and digested with restriction enzymes EcoRI and HindIII to identify the presence of cloned deoD gene fragments. The identified pDEO plasmids were digested with restriction enzymes EcoRI and HindIII and bands of about 720 bp were resolved on 0.8% agarose gel. Meanwhile, plasmids pUG6 (U. Guldenre et al, A new efficient gene disruption cassette for repeated use in budding yeast. Nucleic Acid Research 24 (13), 1996, pp 2519-2524) were digested with restriction enzymes EcoR V and Hinc II to obtain loxp site-containing kanamycin resistance gene fragments (about 1.7 kb). The DNA fragments contained in the bands were ligated into the loxp site-containing kanamycin resistance gene fragments by blunt-end ligation to obtain recombinant plasmids, pTdeoD::loxpKAT (about 4.5 kb) (see FIG. 1B).

After the pTdeoD::loxpKAT recombinant plasmids were transformed into *E. coli* DH5 α, the obtained transformants were smeared onto solid media containing ampicillin and kanamycin (50 mg/L for each) and cultured at 37° C. overnight. Colonies grown on the solid media were inoculated by loop transfer needles onto 3 mL of liquid media containing ampicillin and kanamycin and cultured overnight. Then, plasmid DNAs were extracted using a QIAGEN mini prep kit (QIAGEN). About 2.3 kb DNA fragments containing the ORFs of deoD genes and the loxpKAT sites were amplified by PCR using the plasmid DNAs as templates and the oligonucleotides as set forth in SEQ ID NOS: 1 and 2 as primers. The PCR was performed at 94° C. for 1 minute for denaturation, 55° C. for 1 minute for annealing, and 68° C. for 1 minute for extension for 35 cycles.

The obtained DNA fragments A deoD::loxpKAT were electroporated into *E. coli* GPU1114 containing a foreign guaA gene, and the obtained transformants were smeared onto solid media containing kanamycin to select colonies.

To remove the antibiotic marker from recombinant strains of the selected colonies, pCP20 plasmids were transformed into the recombinant strains of the selected colonies, and the resultant transformants were smeared onto solid media containing ampicillin (50 mg/L) and cultured at 30° C. overnight. Colonies grown on the solid media were toothpicked to ampicillin-containing solid media, kanamycin-containing solid media, and antibiotic-free solid media and cultured at 43° C. overnight. Colonies grown only on the antibiotic-free solid media were harvested. The colonies were designated E. coli DKO-ud and deposited in the Korean Culture Center of Microorganisms (KCCM) on Nov. 30, 2004 (Accession No. KCCM-10633).

Example 2

Construction of Recombinant Plasmid and Inactivation of aphA Gene Using the Recombinant Plasmid About 714 bp DNA fragments containing the ORFs of aphA genes were amplified by PCR using genomic DNAs extracted from the E. coli DKO-ud obtained in Example 1 as templates and oligonucleotides as set forth in SEQ ID NOS: 3 and 4 as primers. The PCR was performed at 94° C. for 30 seconds for denaturation, 55° C. for 30 seconds for annealing, and 68° C. for 1 minute and 30 seconds for extension for 35 cycles.

Figure 2A:
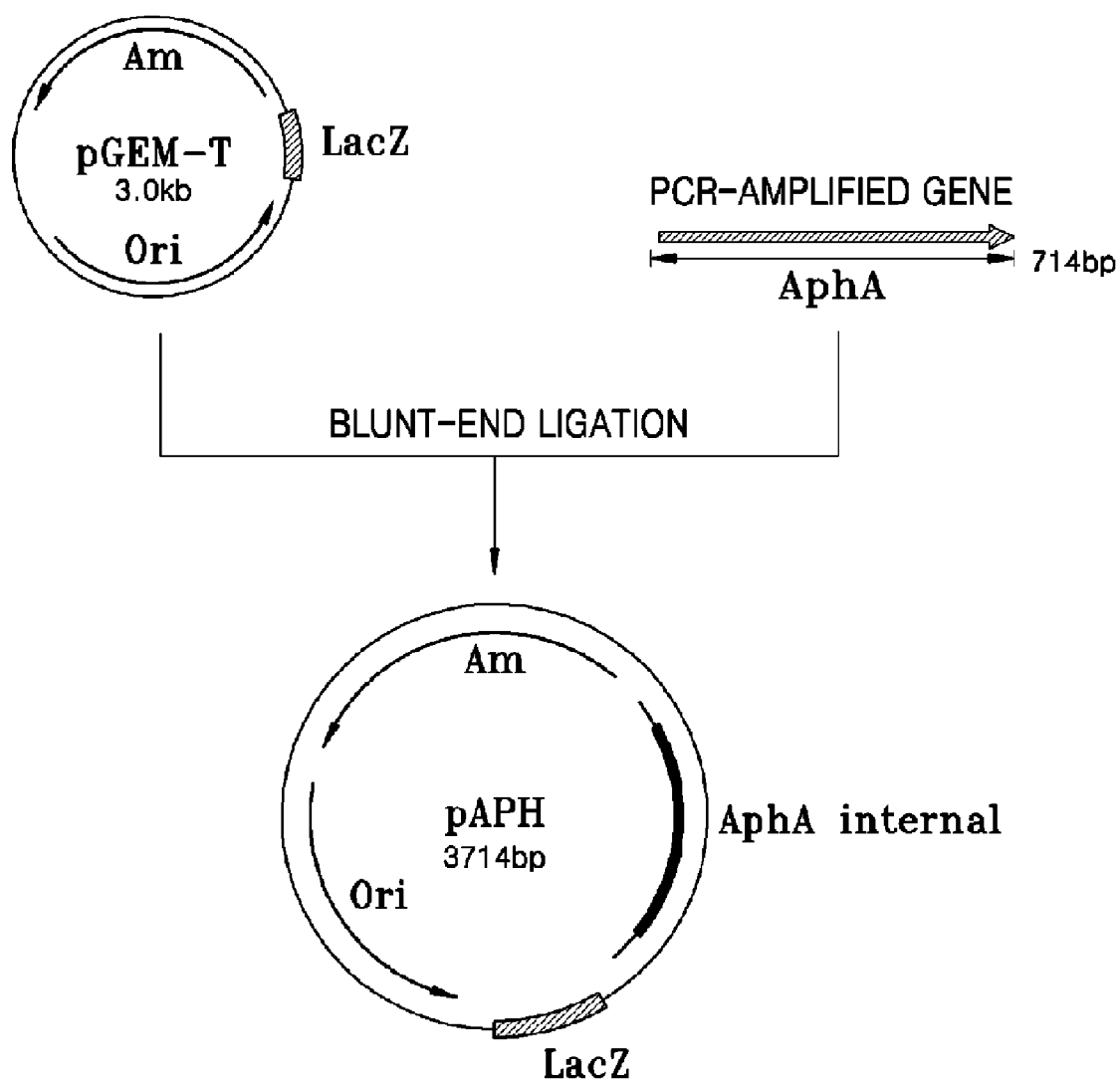
FIG. 2A is a scheme of the construction of a recombinant plasmid pAPH of Example 2 of the present invention.

After the PCR products were size-fractionated by 0.1% agarose gel electrophoresis, bands containing 714 bp DNA fragments were purified. The DNA fragments were ligated into pGEM-T-easy cloning vectors (Promega Co.) at 16° C. overnight (see FIG. 2A). The resultant recombinant plasmids pAPH were transformed into E. coli DH5 α, the obtained transformants were smeared onto solid media containing ampicillin (50 mg/L) and cultured at 37° C. overnight.

Figure 2B:
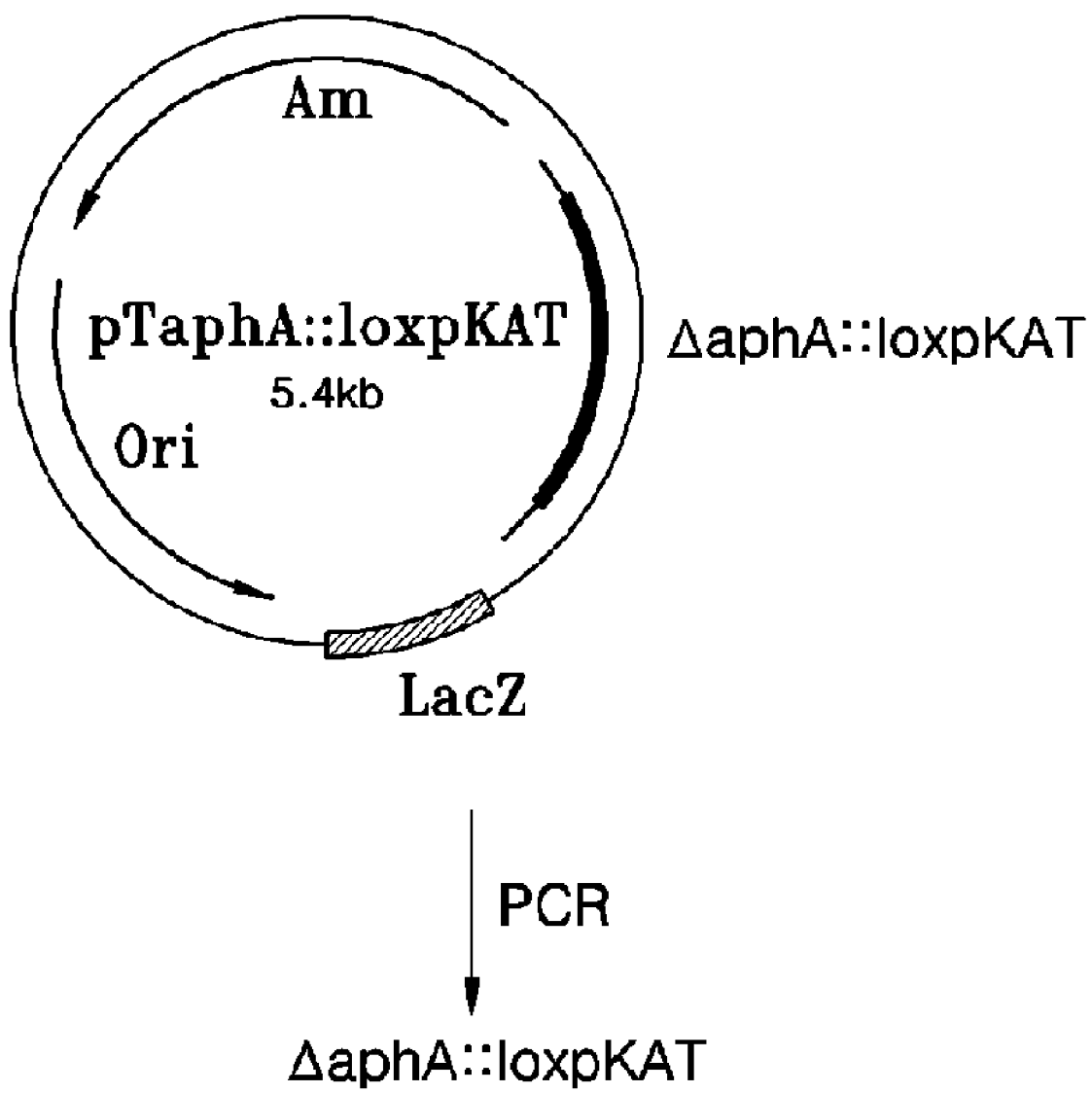
FIG. 2B is a scheme of the construction of a recombinant plasmid pTaphA:loxpKAT of Example 2 of the present invention.

Colonies grown on the solid media were inoculated by loop transfer needles onto 3 mL of ampicillin-containing liquid media and cultured overnight. Then, plasmid DNAs were isolated using a QIAGEN mini prep kit (QIAGEN) and digested with restriction enzyme ClaI to identify the presence of cloned aphA gene fragments. The identified pAPH plasmids were digested with restriction enzyme ClaI and bands of about 3.7 kb were resolved on 0.8% agarose gel. The DNA fragments contained in the bands were blunt-ended with T4 polymerase. Meanwhile, plasmids pUG6 were digested with restriction enzymes EcoRV and HincII to obtain loxp site-containing kanamycin resistance gene fragments (about 1.7 kb). The blunt-ended DNA fragments were ligated into the loxp site-containing kanamycin resistance gene fragments by blunt-end ligation to obtain recombinant plasmids, pTaphA::loxpKAT (about 5.4 kb) (see FIG. 2B).

After the pTaphA::loxpKAT recombinant plasmids were transformed into E. coli DH5 α, the obtained transformants were smeared onto solid media containing ampicillin and kanamycin (50 mg/L for each) and cultured at 37° C. overnight. Colonies grown on the solid media were inoculated by loop transfer needles onto 3 mL of liquid media containing ampicillin and kanamycin and cultured overnight. Then, plasmid DNAs were extracted using a QIAGEN mini prep kit (QIAGEN). About 2.4 kb DNA fragments containing the ORFs of aphA genes and the loxpKAT sites were amplified by PCR using the plasmid DNAs as templates and the oligonucleotides as set forth in SEQ ID NOS: 3 and 4 as primers. The PCR was performed at 94° C. for 1 minute for denaturation, 55° C. for 1 minute for annealing, and 68° C. for 1 minute for extension for 35 cycles.

The obtained DNA fragments A aphA::loxpKAT were electroporated into the E. coli DKO-ud obtained in Example 1, and the resultant transformants were smeared onto solid media containing kanamycin to select colonies.

To remove the antibiotic marker from recombinant strains of the selected colonies, pCP20 plasmids were transformed into the recombinant strains of the selected colonies, and the resultant transformants were smeared onto solid media containing ampicillin (50 mg/L) and cultured at 30° C. overnight. Colonies grown on the solid media were toothpicked to ampicillin-containing solid media, kanamycin-containing solid media, and antibiotic-free solid media and cultured at 43° C. overnight. Colonies grown only on the antibiotic-free solid media were harvested. The colonies were designated E. coli TKO-udh and deposited in the KCCM on Nov. 30, 2004 (Accession No. KCCM-10631).

Example 3

Construction of Recombinant Plasmid and Inactivation of appA Gene Using the Recombinant Plasmid About 1.3 kb DNA fragments containing the ORFs of appA genes were amplified by PCR using the genomic DNAs extracted from the E. coli DKO-ud obtained in Example 1 as templates and oligonucleotides as set forth in SEQ ID NOS: 5 and 6 as primers. The PCR was performed at 94° C. for 30 seconds for denaturation, 55° C. for 30 seconds for annealing, and 68° C. for 1 minute and 30 seconds for extension for 35 cycles.

Figure 3A:
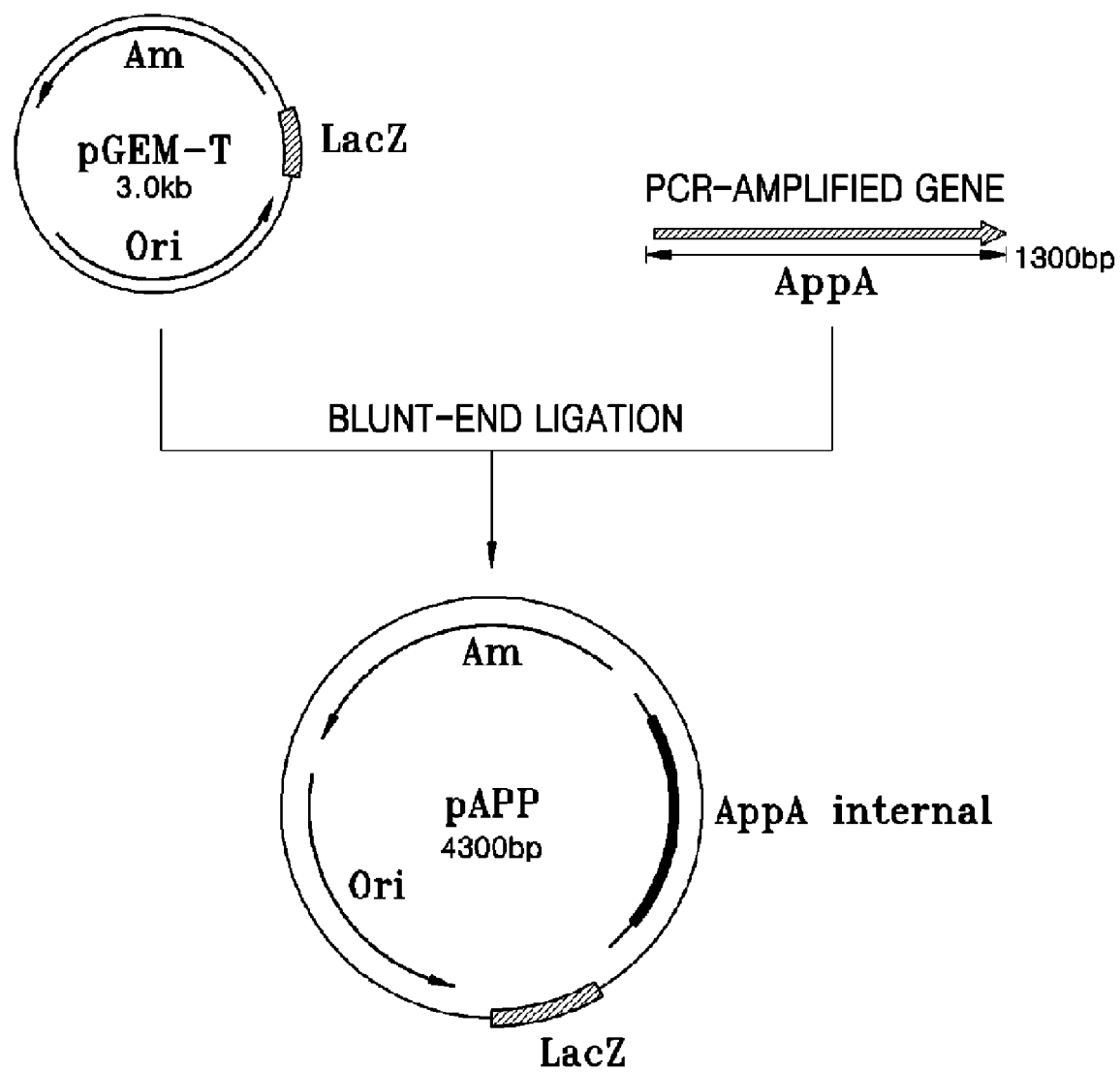
FIG. 3A is a scheme of the construction of a recombinant plasmid pAPP of Example 3 of the present invention.

After the PCR products were size-fractionated by 0.1% agarose gel electrophoresis, bands containing 1.3 kb DNA fragments were purified. The DNA fragments were ligated into pGEM-T-easy cloning vectors at 16° C. overnight (see FIG. 3A). The resultant recombinant plasmids pAPP were transformed into E. coli DH5 α, the obtained transformants were smeared onto solid media containing ampicillin (50 mg/L) and cultured at 37° C. overnight.

Figure 3B:
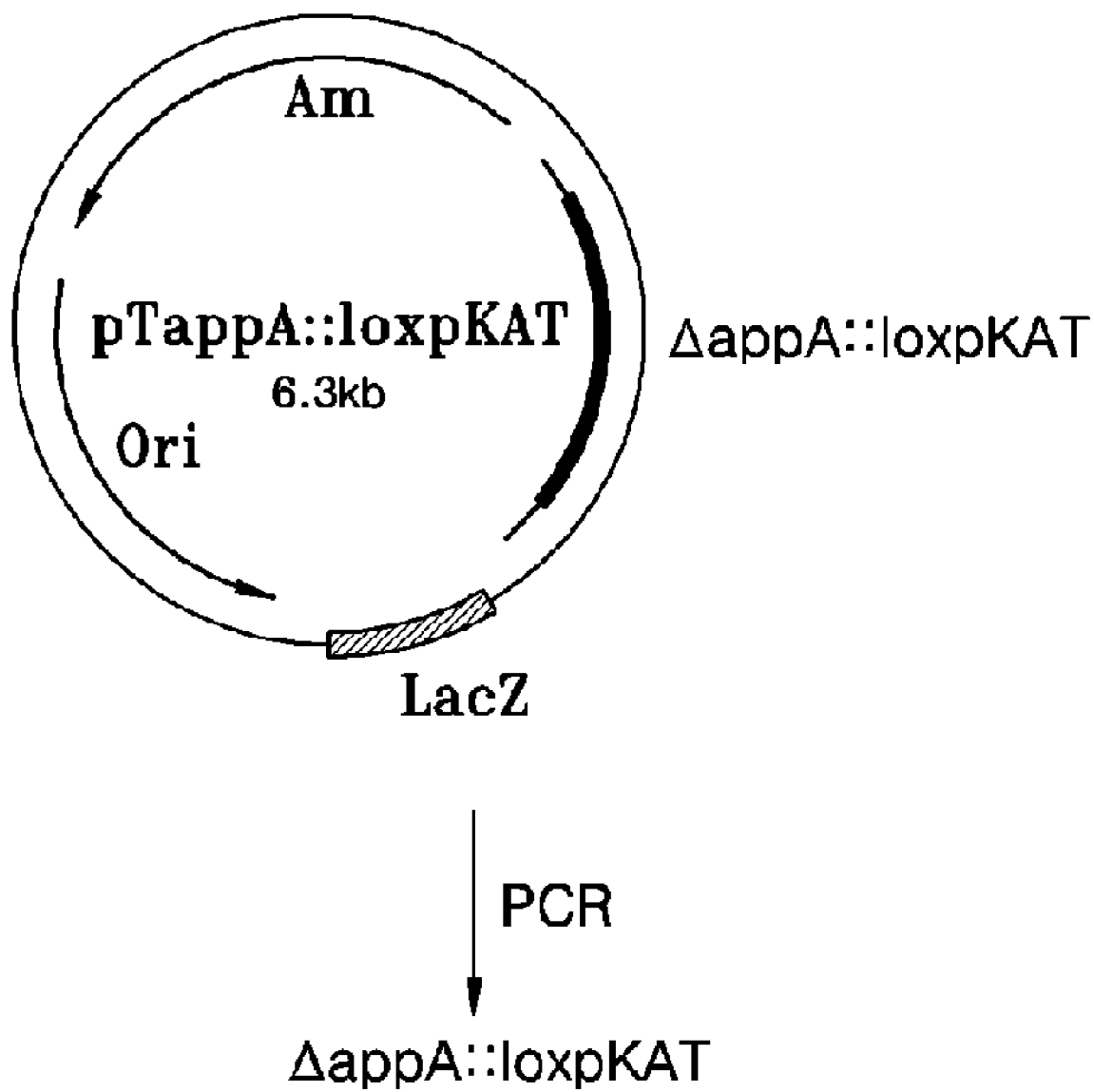
FIG. 3B is a scheme of the construction of a recombinant plasmid pTappA:loxpKAT of Example 3 of the present invention.

Colonies grown on the solid media were inoculated by loop transfer needles onto 3 mL of ampicillin-containing liquid media and cultured overnight. Then, plasmid DNAs were isolated using a QIAGEN mini prep kit (QIAGEN) and digested with restriction enzyme ClaI to identify the presence of cloned appA gene fragments. The identified pAPP plasmids were digested with restriction enzyme BclI and bands of about 4.3 kb were resolved on 0.8% agarose gel. The DNA fragments contained in the bands were blunt-ended with T4 polymerase. Meanwhile, plasmids pUG6 were digested with restriction enzymes EcoRV and HincII to obtain loxp site-containing kanamycin resistance gene fragments (about 1.7 kb). The blunt-ended DNA fragments were ligated into the loxp site-containing kanamycin resistance gene fragments by blunt-end ligation to obtain recombinant plasmids, pTappA::loxpKAT (about 6.3 kb) (see FIG. 3B).

After the pTappA::loxpKAT recombinant plasmids were transformed into E. coli DH5 α, the obtained transformants were smeared onto solid media containing ampicillin and kanamycin (50 mg/L for each) and cultured at 37° C. overnight. Colonies grown on the solid media were inoculated by loop transfer needles onto 3 mL of liquid media containing ampicillin and kanamycin and cultured overnight. Then, plasmid DNAs were extracted using a QIAGEN mini prep kit (QIAGEN). About 3.1 kb DNA fragments containing the ORFs of appA genes and the loxpKAT sites were amplified by PCR using the plasmid DNAs as templates and the oligonucleotides as set forth in SEQ ID NOS: 5 and 6 as primers. The PCR was performed at 94° C. for 1 minute for denaturation, 55° C. for 1 minute for annealing, and 68° C. for 1 minute for extension for 35 cycles.

The obtained DNA fragments A appA::loxpKAT were electroporated into the *E. coli* DKO-udh obtained in Example 2, and the resultant transformants were smeared onto solid media containing kanamycin to select colonies.

To remove the antibiotic marker from recombinant strains of the selected colonies, pCP20 plasmids were transformed into the recombinant strains of the selected colonies, and the resultant transformants were smeared onto solid media containing ampicillin (50 mg/L) and cultured at 30° C. overnight. Colonies grown on the solid media were toothpicked to ampicillin-containing solid media, kanamycin-containing solid media, and antibiotic-free solid media and cultured at 43° C. overnight. Colonies grown only on the antibiotic-free solid media were harvested. The colonies were designated QKO-udhp and deposited in the KCCM on Nov. 30, 2004 (Accession No. KCCM-10632).

Example 4

Construction of Recombinant Plasmid and Inactivation of hprt Gene Using the Recombinant Plasmid About 1.7 kb DNA fragments containing the ORFs of hprt genes were amplified by PCR using genomic DNAs extracted from the *E. coli* QKO-udhp obtained in Example 3 as templates and oligonucleotides as set forth in SEQ ID NOS: 7 and 8 as primers. The PCR was performed at 94° C. for 30 seconds for denaturation, 69° C. for 30 seconds for annealing, and 72° C. for 1 minute and 30 seconds for extension for 30 cycles.

Figure 4A:
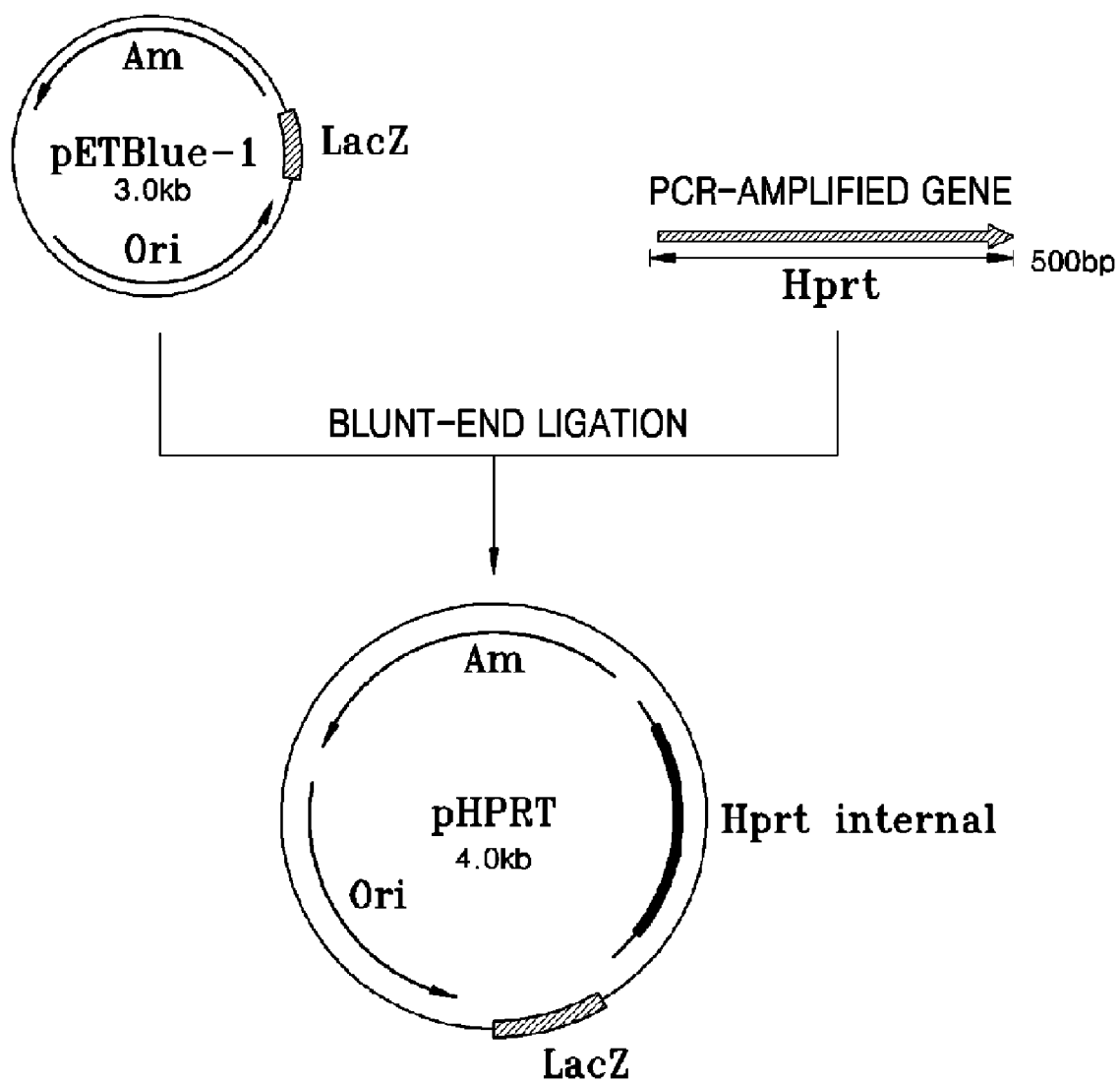
FIG. 4A is a scheme of the construction of a recombinant plasmid pHPRT of Example 4 of the present invention.

After the PCR products were size-fractionated by 0.1% agarose gel electrophoresis, bands containing 500 bp DNA fragments were purified. The DNA fragments were ligated into pETBlue-1 cloning vectors (Novagen Co.) at 16° C. overnight (see FIG. 4A). The resultant recombinant plasmids pHPRT were transformed into *E. coli* DH5 α, the obtained transformants were smeared onto solid media containing ampicillin (50 mg/L) and cultured at 37° C. overnight.

Figure 4B:
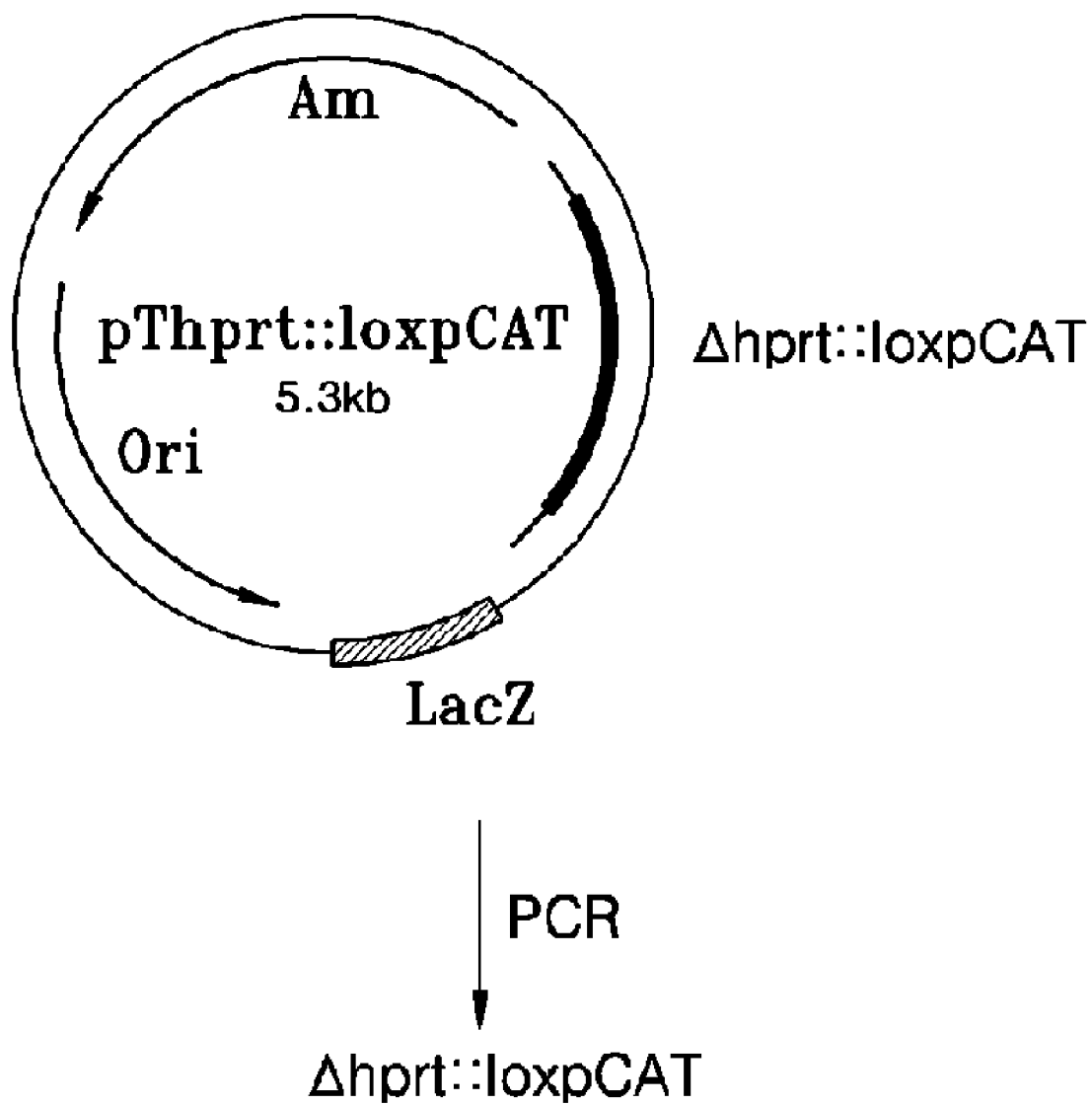
FIG. 4B is a scheme of the construction of a recombinant plasmid pThprt:loxpCAT of Example 4 of the present invention.

Colonies grown on the solid media were inoculated by loop transfer needles onto 3 mL of ampicillin-containing liquid media and cultured overnight. Then, plasmid DNAs were isolated using a QIAGEN mini prep kit (QIAGEN) and digested with restriction enzyme HindII to identify the presence of cloned hprt gene fragments. The identified pHPRT plasmids were digested with restriction enzyme HindII and bands of about 4.0 kb were resolved on 0.7% agarose gel. Meanwhile, plasmids pUG6 were digested with restriction enzymes EcoRV and HincII to obtain loxp site-containing kanamycin resistance gene fragments (about 1.7 kb). The DNA fragments contained in the bands were ligated into the loxp site-containing kanamycin resistance gene fragments by blunt-end ligation to obtain recombinant plasmids, pThprt::loxpCAT (about 5.3 kb) (see FIG. 4B).

After the pThprt::loxpCAT recombinant plasmids were transformed into *E. coli* DH5 α, the obtained transformants were smeared onto solid media containing ampicillin and kanamycin (50 mg/L for each) and cultured at 37° C. overnight. Colonies grown on the solid media were inoculated by loop transfer needles onto 3 mL of liquid media containing ampicillin and kanamycin and cultured overnight. Then, plasmid DNAs were extracted using a QIAGEN mini prep kit (QIAGEN). About 2.1 kb DNA fragments containing the ORFs of hprt genes and the loxpKAT sites were amplified by PCR using the plasmid DNAs as templates and the oligonucleotides as set forth in SEQ ID NOS: 7 and 8 as primers. The PCR was performed at 94° C. for 1 minute for denaturation, 60° C. for 1 minute for annealing, and 72° C. for 1 minute for extension for 30 cycles. The obtained DNA fragments Δ hprt::loxpCAT were electroporated into the *E. coli* QKO-udhp obtained in Example 3, and the resultant transformants were smeared onto solid media containing chloramphenicol to select colonies. The colonies were designated QIKO and deposited in the KCCM on Nov. 30, 2004 (Accession No. KCCM-10630).

Example 5

GMP Productivity of *E. coli* QIKO of Example 4

Among the *E. coli* QIKO colonies selected after smearing on the solid media containing chloramphenicol in Example 4, 30 colonies were cultured in Erlenmeyer flasks containing GMP-producing media with the medium composition of Table 1 below, and GMP production was evaluated. First, the 30 single colonies were cultured overnight in a 32° C. incubator containing GMP-producing solid media. Then, one loopful of each of the single colonies was inoculated on 50 ml of the GMP-producing media and cultured for 7 hours at 37° C. with shaking at 250 rpm. Then, the cell cultures were supplemented with 2% xylene to facilitate the cell membrane permeation of enzymes, substrates, and products in the cell cultures. The resultant cultures were added to enzymatic reaction solutions and incubated at 42° C. for 15 minutes with shaking at 250 rpm. The concentration of GMP was determined by HPLC (high performance liquid chromatography) and the results are presented in Table 2 below.

TABLE 1

| Medium composition for GMP production. | |
| --- | --- |
| Composition | Concentration (g/L) |
| Bacto-peptone | 16 |
| NaCl | 5 |
| Yeast extract | 10 |
| pH 7.0 | |

TABLE 2

| Flask test results for recombinant strains. | | | | | |
| --- | --- | --- | --- | --- | --- |
| | Strain | | | | |
| | GPU1114 | DKO-ud | TKO-udh | QKO-udhp | QIKO |
| GMP (U/mL) | 46 | 46 | 46 | 47 | 49 |

As shown in Table 2, the parent strains GPU1114 produced 46 U/mL of GMP, whereas the recombinant strains QIKO, in which the genes with nucleotide degradability were inactivated, produced 49 U/mL of GMP. As seen from the above results, the recombinant strains QIKO of the present invention exhibited 6% higher GMP production than the parent strains.

Example 6

Comparison of GMP Byproduct (Guanine and Guanosine) Production for Recombinant Strains in Erlenmeyer Flasks The *E. coli* QIKO colonies selected after smearing on the solid media containing chloramphenicol in Example 4 were cultured in Erlenmeyer flasks containing GMP-producing media with the medium composition of the above Table 1. The cultures were added to reaction solutions for GMP byproduct production with the composition of Table 3 below and byproduct production was evaluated.

First, the *E. coli* QIKO single colonies were cultured overnight in a 32° C. incubator containing GMP-producing solid media. Then, one loopful of each of the single colonies was inoculated on 50 ml of the GMP-producing media and cultured for 7 hours at 37° C. with shaking at 250 rpm. Then, the cell cultures were supplemented with 2% xylene to facilitate the cell membrane permeation of enzymes, substrates, and products in the cell cultures, and incubated at 37° C. for 20 minutes with shaking at 250 rpm. The resultant cultures were mixed with the reaction solutions for GMP byproduct production with the composition of Table 3 and incubated at 42° C. for 8 hours with shaking at 250 rpm. The concentration of two types of byproducts, guanine and guanosine, with respect to time was determined by HPLC, and the results are presented in Table 4 below.

TABLE 3

Reaction solution composition for GMP byproduct production.

| Composition | Concentration (g/L) |
| --- | --- |
| 800 mM tris-maleate | 24.20 |
| MgSO4 | 4.92 |
| (NH4)2SO4 | 6.60 |
| XMP | 15.65 |
| GMP | 11.54 |
| pH 7.0 | |

TABLE 4

Results of byproduct production test for recombinant strains.

| | Strain | | | | |
| --- | --- | --- | --- | --- | --- |
| | GPU1114 | DKO-ud | TKO-udh | QKO-udhp | QIKO |
| GMP degradation (mmol) | 2.54 | 2.11 | 2.00 | 1.70 | 1.37 |
| GMP degradation (%) | 100 | 83 | 77 | 67 | 53 |

As shown in Table 4, the concentration of degraded GMP for the parent strains GPU1114 was 2.54 mmol, whereas the concentration of degraded GMP for the recombinant strains QIKO, in which the genes with nucleotide degradability were inactivated, was 1.37 mmol. That is, the GMP degradation of the recombinant strains QIKO was reduced by about 47% relative to that of the parent strains.

As described above, GMP-producing strains of the present invention exhibit high conversion efficiency of XMP to GMP and low GMP degradation activity.

According to a method of accumulating GMP synthetase in cells of the present invention, GMP synthetase can be accumulated in a high concentration in cells.

According to a method of producing GMP, GDP, or GTP of the present invention, GMP, GDP, or GTP can be produced in high efficiency.

The invention claimed is:

1. An isolated strain of the genus *Escherichia* obtained by inactivation of the endogenous deoD, aphA, and appA genes of the strain *Escherichia* sp. GPU1114 deposited with Korean Culture Center of Microorganisms (KCCM) as Accession No. KCCM-10536, wherein said inactivation is by homologous recombination-based substitution.

2. The isolated strain of claim 1, wherein the strain is *Escherichia* sp. QKO-udhp deposited with Korean Culture Center of Microorganisms (KCCM) as Accession No. KCCM-10632.

3. The isolated strain of claim 1, wherein an endogenous hprt gene is further inactivated.

4. The isolated strain of claim 1, wherein the strain is *Escherichia* sp. QIKO-udhp deposited with Korean Culture Center of Microorganisms (KCCM) as Accession No. KCCM-10630.

5. A method of accumulating 5'-guanylic acid (GMP) synthetase in cells, the method comprising culturing the strain of claim 1.

6. A method of accumulating 5'-guanylic acid (GMP) synthetase in cells, the method comprising culturing the strain of claim 2.

7. A method of accumulating 5'-guanylic acid (GMP) synthetase in cells, the method comprising culturing the strain of claim 3.

8. A method of accumulating 5'-guanylic acid (GMP) synthetase in cells, the method comprising culturing the strain of claim 4.

9. The isolated strain of claim 1, wherein an endogenous glnL gene is inactivated, a guaA gene encoding 5'-xanthylic acid (XMP) aminase is inserted by transformation, and an endogenous ushA gene encoding 5'-nucleotidase is inactivated.

10. A method of producing 5'-guanylic acid (GMP), guanosine 5'-diphosphate (GDP), or guanosine 5'-triphosphate (GTP), the method comprising culturing the strain of claim 1.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
atggctaccc cacacattaa t                    21

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
ctttatcgcc cagcagaacg g                    21

```
<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tcaacatact gactatttag g                                         21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ctctgtcagt attctgaatt g                                         21

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
cggcgcatta gcatcgca                                             18

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ttcaggtaac tgaatgctct t                                         21

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
atggttagag atatgaaa                                             18

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ttactcgtcc agcagaatca c                                         21
```